US005785355A

United States Patent [19]

Main

[11] Patent Number: 5,785,355

[45] Date of Patent: Jul. 28, 1998

[54] SINGLE UNIT PHONE CARD ASSEMBLY AND METHOD OF PRODUCING SAME

[75] Inventor: George W. Main, Essex Junction, Vt.

[73] Assignee: KoBel, Inc., Milton, Vt.

[21] Appl. No.: 752,655

[22] Filed: Nov. 19, 1996

[51] Int. Cl.$^6$ .............................. B42D 15/00; A61F 13/02

[52] U.S. Cl. .......................... 283/108; 428/40.1; 283/102; 283/56

[58] Field of Search .............................. 283/108, 56, 102; 428/40.1, 41.7, 41.8, 42.1, 42.3, 201

[56] References Cited

U.S. PATENT DOCUMENTS

| | | | |
|---|---|---|---|
| 3,420,364 | 1/1969 | Kennedy, Jr. . | |
| 4,653,775 | 3/1987 | Raphael et al. | 283/108 |
| 4,804,827 | 2/1989 | Jung | 283/108 |
| 4,872,707 | 10/1989 | de Bruin . | |
| 4,897,533 | 1/1990 | Lyszczarz . | |
| 4,911,477 | 3/1990 | Shishido | 283/81 |
| 5,019,436 | 5/1991 | Schramer et al. | 283/56 |
| 5,042,842 | 8/1991 | Green et al. | 283/81 |

*Primary Examiner*—Larry I. Schwartz
*Assistant Examiner*—Tisa Stewart
*Attorney, Agent, or Firm*—Thomas N. Neiman

[57] ABSTRACT

The present invention is directed to a card structure which is a single unit phone card assembly which provides an area to provide variable information which will maintain the variable information in a hidden area until the information is exposed by the removal of an overlamination and allow the card to be detached to be used as a phone card. The phone card is comprised of two layers of material upon which a variable image printed message is applied. A pattern of silicone is positioned on the face of the top sheet and a pattern of varnish is positioned on the bottom of the top sheet. Adhesive is then used on the face of the base sheet and the sheets are slit and crossed over and laminated together. A series of die cuts and laminations are done to finish the card and extra material is stripped away. In use, the consumer will receive the card as a single unit and peel away the overlamination in order to remove the card to reveal the necessary information to make the telephone call. No additional materials or protections are necessary. A method of producing the multiple layered cards is also disclosed.

7 Claims, 2 Drawing Sheets

SINGLE UNIT PHONE CARD ASSEMBLY AND METHOD OF PRODUCING SAME

BACKGROUND OF THE INVENTION

This invention pertains to card type devices, and in particular, to such a single unit phone cards that are designed to allow the user to receive a single unit phone card having the vital information kept under wraps until such time as the user wishes to use the information. A method of producing a single unit phone card assembly is also disclosed.

Many types of phone cards or collector cards are currently on the market. Most current cards are manufactured as a plain card having all the necessary information. The card is then enclosed in a wrap of cellophane or the like, so that the specific information and the magnetic strip necessary for the call is kept hidden until such time as it is used. What is needed is a single unit phone card assembly that will provide a simplified delivery system for the cards and not reveal the information nor the magnetic strip on the card until it is sought by the user. What has not been done in this area is a single piece item that can be in the form of a phone card that can contain important information on the sealed portion of the phone card that has been laminated together and, at the same time, can easily have sections removed to reveal that information. What is needed is a single unit phone card assembly that an individual can easily and effectively print on current printing equipment while, at the same time, maintaining a designated finished phone card size. What is also needed is a single unit phone card assembly which will allow a variable imaging printing capability upon any of the sides of the single unit phone card assembly.

Clearly, it is desirable for a item of this type to be very adaptable. At the same time, the item should be easy to manufacture and be produced of cost effective material. It is the object of this invention to set forth a single unit phone card assembly which avoid the disadvantages, previously mentioned limitations of typical phone card delivery systems.

SUMMARY OF THE INVENTION

Particularly, it is the object of this invention to teach a single unit phone card assembly, for use in situations that require the use of the card that can be peeled apart to reveal additional information to the user without using additional materials to deliver the assembly to the user, comprising multiple sheets of material; said multiple sheets of material having a primary sheet containing a face side and a rear side, said front side and said rear side having a plurality of printable areas for variable image printing of any desired information such as dialing information and code numbers or the like; said multiple sheets of information further having a secondary sheet containing a face side and rear side, the face side and the rear side having a plurality of printable areas for variable image printing of any desired information such as dialing information and code numbers or the like; release agent means positioned in predetermined areas on said face side of said primary sheet as desired; a pattern of varnish positioned on said rear side of said primary sheet as desired; attaching means positioned in predetermined areas on said face side of said primary sheet; said primary sheet having slits cut thereon; said primary sheet and said secondary sheet comprising a single entity by being laminated together transferring said attaching means to said opposite sheet; and a covering of material positioned over said assembly and laminated thereon.

It is also the object of this invention to teach a method of producing a single unit phone card assembly, for use in situations that require the use of an item that can be peeled apart and reveal additional information to the user without using any additional materials to deliver the assembly to the user, comprising the steps of providing sheets of material, a primary sheet and a secondary sheet, each of said sheets having a face side and a rear side; printing said primary sheet of material on any of the sides as desired for the purposes of the specific item; applying a coating of release agent on the face side of the primary sheet in a predetermined fashion in order to facilitate separation of the sheets of materials when desired; applying a pattern of varnish on the rear side of the primary sheet in a predetermined fashion; applying an adhesive layer on the face side of the secondary sheet in a predetermined fashion; slitting and crossing over said primary sheet and said secondary sheet; laminating of the sheets together transferring the adhesive layer into the position desired; internally cutting of the primary sheet of said assembly; overlaying a layer of material over said assembly; externally cutting said assembly as desired to create the external dimensions of the assembly; and stripping excess material from said assembly.

BRIEF DESCRIPTION OF THE INVENTION

Further objects and features of this invention will become more apparent by reference to the following description taken in conjunction with the following figures, in which.

DESCRIPTION OF THE PREFERRED EMBODIMENTS

Figure 1:
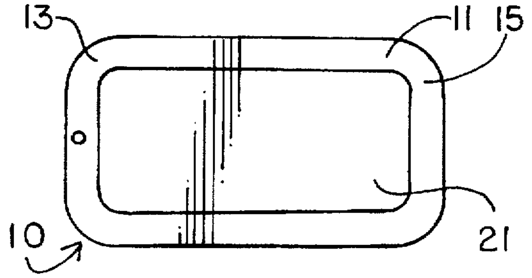
FIG. 1 is a bottom plan view of the primary sheet of the single unit phone card assembly.
Figure 2:
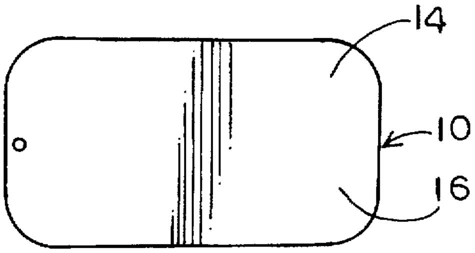
FIG. 2 is a bottom plan view of the secondary sheet thereof.
Figure 3:
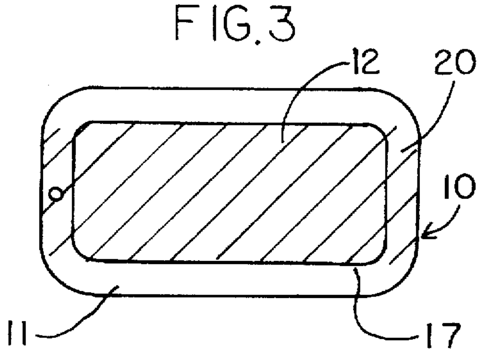
FIG. 3 is top plan view of the primary sheet of the single unit phone card assembly.
Figure 4:
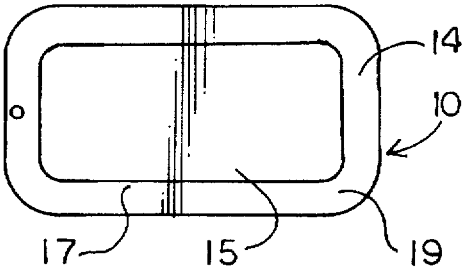
FIG. 4 is a top plan view of the secondary sheet thereof.
Figure 5:
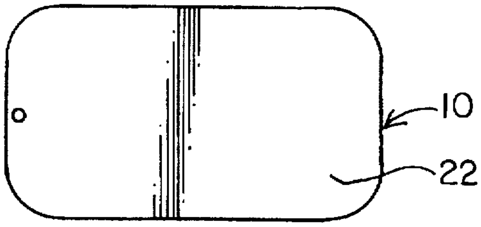
FIG. 5 is a top plan view of the overlay material.
Figure 6:
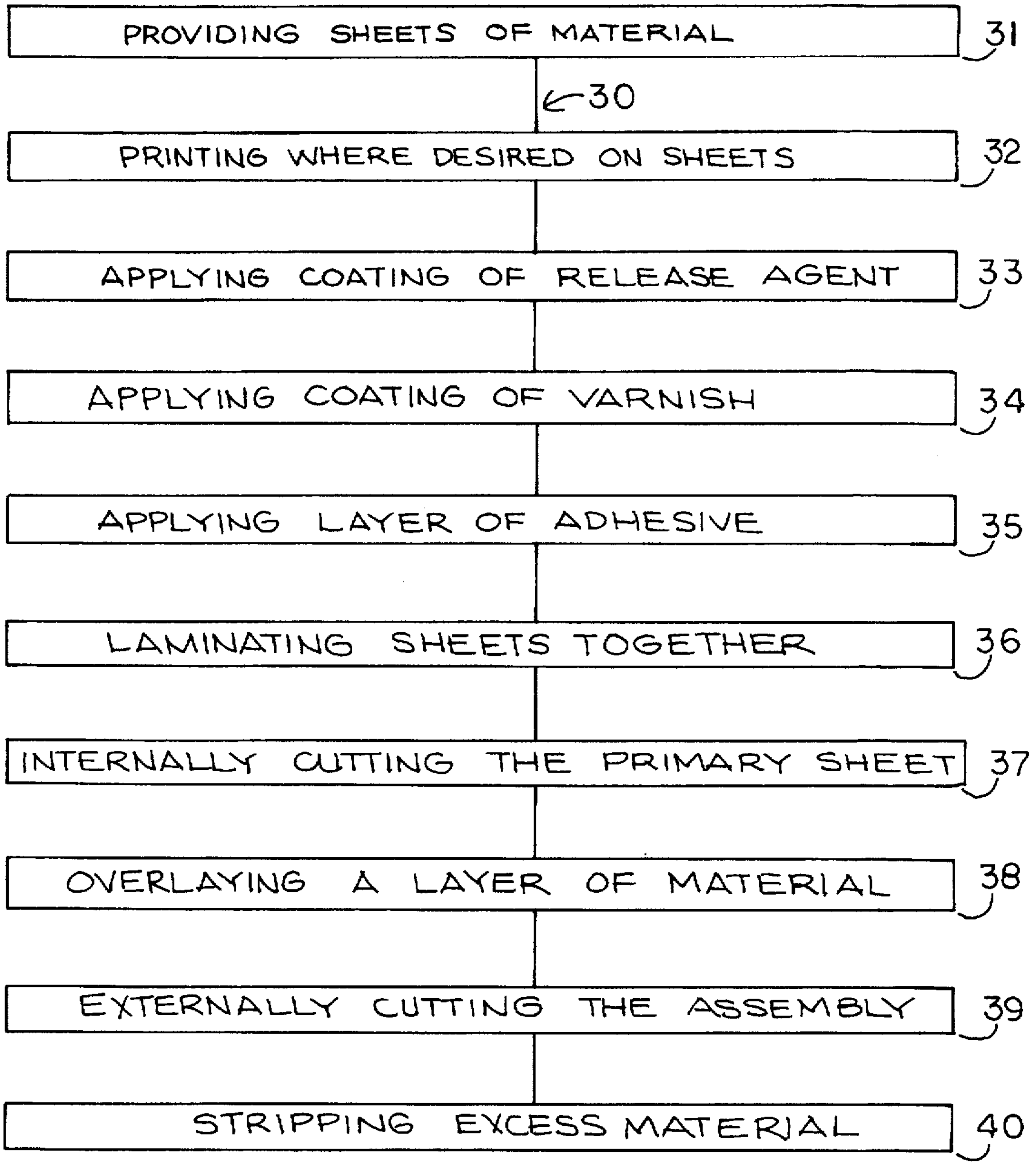
FIG. 6 is a block diagram showing the novel method of producing a single unit phone card assembly.

As shown in the figure, the novel single unit phone card assembly 10 comprises a primary sheet 11 having a face side 12 and a rear side 13. The front side 12 and the rear side 13 have a plurality of printable areas upon which variable imagining information such as numbers or magnetic strips may be printed. A secondary sheet 14 is provided having a face side 15 and a rear side 16 upon which there are a plurality of printable areas that instructions, personalized information or the like can be printed thereon depending on what the specific requirements of the particular card happen to be. It is also possible to print specific variable information to be printed on any side of the card. The face side 15 of the secondary sheet 14 have a layer of adhesive 19 applied in a predetermined pattern (shown around the edge of the sheet) depending upon the specific requirements of the particular card.

A release agent such as a coating of silicone 20 would be applied in predetermined areas (shown in the central area of the secondary sheet) of the face side 12 of the primary sheet 11 and the rear side 13 of the primary sheet 11 is coated with a dry strippable varnish 21 (shown in the central area of the secondary sheet). The pattern used with the release agent will be matched up with the adhesive patterns to facilitate the opening of areas of the card assembly 10. The release agent application and the application of the varnish would be limited to those areas where opening is desired, not the whole card. A die cut 17 of the primary sheet is performed, which in combination with the position of the silicone 20 and varnish 21 specify the areas to be visible when opened. The sheets 11 and 14 are then laminated together. This can be accomplished by slitting and crossing over the web of material or by using two webs of material. The pattern of adhesive is transferred onto the proper position on the other sheet during the lamination process. A sheet of plastic film 22 is then laminated over the entire assembly 10 creating the finished product.

The novel method 30 of producing single unit phone cards comprises the following steps: providing a sheets of material, a primary sheet and a secondary sheet, each having a face side and a rear side 31; printing said primary sheet of material on any of the sides as desired for the purposes of the specific item 32; applying a coating of a release agent on the face side of the primary sheet in order to facilitate separation of the sheets of material when desired 33; applying a pattern of varnish on the rear side of the primary sheet in a predetermined fashion 34; applying a layer of adhesive on the face side of the secondary sheet in a predetermined fashion 35; laminating said sheets together transferring the layer of adhesive into the position desired 36; internally cutting of the primary sheet of said assembly 37; overlaying a layer of material over said assembly 38; externally cutting said assembly as desired to create the external dimensions of the assembly 39; and stripping excess material from the assembly 40.

The release agent, the varnish and the adhesive can be applied in a manner that will determine those areas of the card that the manufacturer wishes to have separated by the consumer. The multiple layers of material can be produced from two separate webs of material or can be produced from a single web that is slit and crossed over onto itself during the process of manufacturing. The overlay material and the primary and secondary sheet are designed to provide security for the card and ease of access for the user when needed. The flexibility provided to the manufacturer afforded by this process allows an infinite number of formats of cards to be produced to meet the demands of the clients.

While I have described my invention in connection with specific embodiments thereof, it is clearly to be understood that this is done only by way of example and not as a limitation to the scope of my invention as set forth in the objects thereof and in the appended claims.

I claim:

1. A single unit phone card assembly, for use in situations that require the use of a card that can be peeled apart to reveal additional information to the user without using additional materials to deliver the single unit phone card assembly to the user, comprising:

multiple sheets of material;

said multiple sheets of material having a primary sheet containing a face side and a rear side, said face side and said rear side having a plurality of printable areas for variable image printing of any desired information such as dialing information and code numbers or the like;

said multiple sheets of material further having a secondary sheet containing a face side and a rear side, the face side and the rear side having a plurality of printable areas for variable image printing of any desired information such as dialing information and code numbers or the like;

release agent means positioned in predetermined areas on said face side of said primary sheet as desired;

a pattern of varnish positioned on said rear side of said primary sheet as desired;

attaching means positioned in predetermined areas on said face side of said secondary sheet;

said primary sheet having slits cut thereon;

said primary sheet and said secondary sheet comprising a single entity by being laminated together and transferring said attaching means of said secondary sheet to said primary sheet; and a covering layer of material positioned over said single unit phone card assembly and laminated thereon.

2. A single unit phone card assembly, according to claim 1, wherein:

said multiple sheets of material comprises a document of cellulose construction; and said multiple sheets of material further comprises a document of plastic construction.

3. A single unit phone card assembly, according to claim 1, wherein:

said release agent means comprises the use of a silicone layer positioned on said face side of said primary sheet as desired for permitting ease of removal of said primary sheet and said secondary sheet.

4. A single unit phone card assembly, according to claim 1, wherein:

said attaching means comprises the use of an adhesive on said face side of said secondary sheet as desired for holding of said multiple sheets together.

5. A single unit phone card assembly, according to claim 1, wherein:

said slits in said primary sheets comprise areas for permitting removal of material for revealing information to the user.

6. A single unit phone card assembly, according to claim 1, wherein:

said lamination of said primary and said secondary sheets comprises pressing said sheets together forming a single entity and transferring said attaching means from one sheet to another sheet.

7. A single unit phone card assembly, according to claim 1, wherein:

said covering layer of material comprises the use of a plastic film over said single unit phone card assembly to seal said single unit phone card assembly.

* * * * *